United States Patent [19]
>
> Hamprecht et al.

[11] Patent Number: 4,726,837

[45] Date of Patent: Feb. 23, 1988

[54] USE OF 4H-PYRIDO[2,3-d]OXAZIN-4-ONE DERIVATIVES FOR CONTROLLING UNDESIRABLE PLANT GROWTH

[75] Inventors: Gerhard Hamprecht, Weinheim; Juergen Varwig, Heidelberg; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 760,643

[22] Filed: Jul. 30, 1985

[30] Foreign Application Priority Data

Aug. 2, 1984 [DE] Fed. Rep. of Germany ....... 3428476

[51] Int. Cl.$^4$ .............................................. A01N 43/84
[52] U.S. Cl. ............................................ 71/94; 544/91
[58] Field of Search ............................... 544/91; 71/94

[56] References Cited

U.S. PATENT DOCUMENTS

| | | | |
|---|---|---|---|
| 3,232,736 | 2/1966 | Seefelder | 71/2.5 |
| 3,914,121 | 10/1975 | Doyle, Jr. | 71/90 |
| 3,970,652 | 7/1976 | Doyle | 260/244 |
| 3,989,698 | 11/1976 | Jacobs et al. | 260/244 |
| 4,315,766 | 2/1982 | Hamprecht et al. | 71/88 |
| 4,379,788 | 4/1983 | Heider et al. | 424/251 |

FOREIGN PATENT DOCUMENTS 1670375 5/1970 Fed. Rep. of Germany.
53-50196 5/1978 Japan.

OTHER PUBLICATIONS

Hurd et al., Journal of Organic Chemistry, vol. 35, No. 5 (May 1970), pp. 1471–1475.
J. Chem. Soc. (c)(1968) 1593.
J. Org. Chem. 9, (1944) 396.

*Primary Examiner*—Richard L. Raymond
*Attorney, Agent, or Firm*—Keil & Weinkauf

[57] ABSTRACT

4H-Pyrido[2,3-d][1,3]oxazin-4-one derivatives of the formula

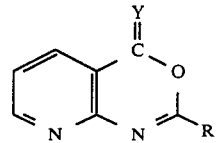

where Y is oxygen or sulfur and R is phenyl which is unsubstituted or substituted by halogen, haloalkyl, haloalkoxy, haloalkylmercapto, haloalkylsulfinyl or haloalkylsulfonyl, are used for controlling undesirable plant growth.

4 Claims, No Drawings

USE OF 4H-PYRIDO[2,3-d][1,3]OXAZIN-4-ONE DERIVATIVES FOR CONTROLLING UNDESIRABLE PLANT GROWTH

The present invention relates to 4H-pyrido[2,3-d][1,3]oxazin-4-one derivatives, herbicides which contain these compounds as active ingredients, and methods of controlling undesirable plant growth with these compounds.

It has been disclosed that substituted 4H-pyrido[2,3-d][1,3]oxazin-4-ones possess pharmacological activity (JP-A No. 50 196/1978) or are suitable intermediates for the preparation of pharmacological active compounds (EP-A No. 54 132). Moreover, 4H-3,1-benzoxazin-4-one derivatives are intermediates for the synthesis of pharmacological active compounds (DE-A Nos. 1 670 375 and 2 556 590) and also possess herbicidal activity (BE-A No. 648 259, U.S. Pat. No. 3,970,652 and EP-A No. 17 931).

We have found that 4H-pyrido[2,3-d][1,3]oxazin-4-one derivatives of the formula Ia

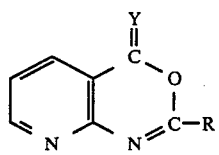
(Ia)

where Y is oxygen or sulfur and R is phenyl which is unsubstituted or o-, m- or p-substituted by halogen, $C_1$–$C_4$-haloalkyl, $C_1$–$C_4$-haloalkoxy, $C_1$–$C_4$-halo-alkylmercapto, $C_1$–$C_4$-haloalkylsulfinyl or $C_1$–$C_4$-haloalkylsulfonyl, not only have a good herbicidal action but also are substantially better tolerated by crop plants compared with herbicides which contain the conventional benzoxazines as active ingredients.

In formula Ia, R is phenyl which is unsubstituted or substituted by fluorine, chlorine, bromine, iodine, trifluoromethyl, 1,1,1-trifluoroethyl, 1,1,1,3,3,3-hexafluoropropyl, chloromethoxy, fluoromethoxy, difluoromethoxy, difluorochloromethoxy, fluorodichloromethoxy, trifluoromethoxy, trichloromethoxy, 1,1,2,2-tetrafluoroethoxy, 1,1,2-trifluoro-2-chloroethoxy, 1,1,2-trifluoro-2-chloroethoxy, 1,1,2-trifluoro-2-bromoethoxy, 1,1,2,3,3,3-hexafluoro-n-propoxy, pentafluoroethoxy, hexafluoroisopropoxy, fluorodichloromethyl, difluorochloromethyl, difluoromethylmercapto, trifluoromethylmercapto, dichlorofluoromethylmercapto, chlorodifluoromethylmercapto, pentafluoroethylmercapto, 1,1,2,2-tetrafluoroethylmercapto, chloromethylsulfonyl, difluoromethylsulfonyl, trifluoromethylsulfonyl, pentafluoroethylsulfonyl or trifluoromethylsulfinyl.

The 4H-pyrido[2,3-d][1,3]oxazin-4-one derivatives of the formula I

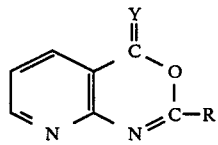
(I)

where Y is oxygen or sulfur and R is phenyl which is o-, m- or p-substituted by halogen, $C_1$–$C_4$-haloalkyl, with the exception of trifluoromethyl, $C_1$–$C_4$-haloalkoxy, $C_1$–$C_4$-haloalkylmercapto, $C_1$–$C_4$-haloalkylsulfinyl or $C_1$–$C_4$-haloalkylsulfonyl, are novel.

The 4H-pyrido[2,3-d][1,3]oxazin-4-one derivatives of the formula I are obtained by a method in which an acid of the formula II

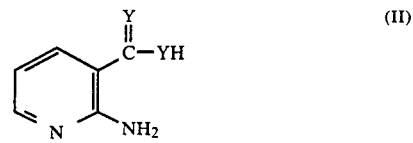
(II)

where Y has the above meanings, is reacted with not less than a two-fold molar excess of an acyl halide of the formula III

(III)

where R has the above meanings and Hal is halogen, preferably fluorine, chlorine or bromine, in particular chlorine, in an aromatic tertiary amine as the solvent, at from 10° to 90° C.

Advantageously, a two-fold excess of an acyl halide of the formula III is run into a solution of an unsubstituted or substituted aminonicotinic acid of the formula II in from 5 to 25 times the molar amount, based on aminonicotinic acid, of an aromatic amine, at from 10° to 60° C., after which the mixture is stirred for a further 30–180 minutes at from 25° to 90° C. (JP-A No. 50 196/1978 and J. Chem. Soc. (C) 1968, 1593). Working up can then be carried out by stirring ice water into the mixture and filtering off under suction the precipitate which separates out. It is also possible for the acyl halide to be initially taken and the aminonicotinic acid of the formula II to be added.

Examples of suitable aromatic tertiary amines are pyridine, α-, β- and γ-picoline, lutidine, quinoline and acridine.

The 4H-pyrido[2,3-d][1,3]oxazin-4-one derivatives of the formula I can furthermore be obtained by a method in which an acid of the formula II

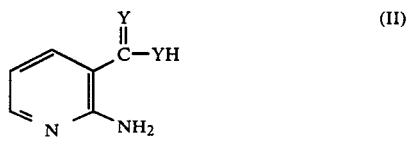
(II)

where Y has the above meanings, or an alkali metal or alkaline earth metal salt of this aminonicotinic acid, is reacted with about the stoichiometric amount of an acyl halide of the formula III

(III)

where R has the above meanings and Hal is halogen, in an inert organic solvent or in water and in the presence or absence of an acid acceptor, at from 0° to 90° C., to give a carboxamide of the formula IV

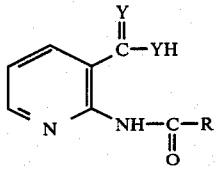

(IV)

where R and Y each have the above meaning, and then cyclizing the product in the presence of a dehydrating agent at from 30° to 150° C.

Suitable inert solvents are hydrocarbons, such as naphtha, gasoline, toluene, pentane, hexane, cyclohexane or petroleum ether, halohydrocarbons, such as methylene chloride, chloroform, carbon tetrachloride, 1,1- and 1,2-dichloroethane, 1,1,1- and 1,1,2-trichloroethane, chlorobenzene, o-, m- and p-dichlorobenzene and o-, m- and p-chlorotoluene, nitrohydrocarbons, such as nitrobenzene, nitroethane and o-, m- and p-chloronitrobenzene, nitriles, such as acetonitrile, butyronitrile and isobutyronitrile, ethers, such as diethyl ether, di-n-propyl ether, tetrahydrofuran and dioxane, esters, such as ethyl acetoacetate, ethyl acetate or isobutyl acetate, and amides, such as formamide, N-methylformamide or N,N-dimethylformamide.

All conventional acid acceptors can be employed. These preferably include alkali metal hydroxides, alkali metal carbonates and tertiary organic bases. Specific examples of particularly suitable compounds are sodium hydroxide, sodium carbonate, sodium bicarbonate, triethylamine, pyridine, trimethylamine, $\alpha$-, $\beta$- and $\gamma$-picoline, butidine, N,N-dimethylaniline, N,N-dimethylcyclohexylamine, quinoline, tri-n-propylamine and tri-n-butylamine. The acid acceptor is advantageously used in an equivalent amount, based on the acyl halide of the formula III.

Suitable dehydrating agents are symmetric and mixed carboxylic anhydrides, such as acetic anhydride, propionic anhydride, butyric anhydride, formic acetic anhydride, formic propionic anhydride, or acetic propionic anhydride, and dicyclohexylcarbodiimide, phosgene, thionyl chloride, phosphorus pentachloride, phosphorus trichloride, phosphorus oxychloride and phosphorus pentoxide. The cyclization is carried out with the addition of from 1 to 10 times the equivalent amount, based on the carboxamide of the formula IV, of a dehydrating agent.

The starting materials of formulae II and III are used in about stoichiometric amounts, i.e. from 0.9 to 1.1 moles of the starting material of the formula III are employed per mole of starting material of the formula II.

Advantageously, the process is carried out so that the acyl halide of the formula III and an equivalent amount of acid acceptor are fed, via two feeds, to about an equivalent amount of the aminonicotinic acid of the formula II, or its salt, in an inert organic solvent or in water, at from 0° to 60° C. The reaction mixture is then stirred for a further 15 minutes to 14 hours at from 20° to 90° C., after which it is evaporated down if necessary, acidified with 5N hydrochloric acid while hot and then cooled, and the product is filtered off under suction (J. Org. Chem. 9 (1944), 396). An N-acyl-2-aminonicotinic acid is obtained. This can be cyclized in the presence of from 5 to 10 times the amount of acetic anhydride by stirring under reflux, if necessary while distilling off the resulting acetic acid, to give the desired 4H-pyrido[2,3-d][1,3]oxazin-4-one derivative. The mixture is worked up by removing excess acetic anhydride in a rotary evaporator under reduced pressure, and, if necessary, the product is purified by recrystallization. Instead of the aminonicotinic acid, it is also possible for the acyl halide to be initially taken.

Instead of carrying out cyclization with acetic anhydride, it can also be effected using an equivalent amount to 4 times the equivalent amount of dicyclohexylcarbodiimide, or phosgene, thionyl chloride, phosphorus pentachloride, phosphorus trichloride, phosphorus oxychloride or phosphorus pentoxide, at from 30° to 150° C.

The 4H-pyrido[2,3-d][1,3]oxazin-4-one derivatives of the formula I can be isolated from the reaction mixture by treating the latter with water, dilute alkali or dilute acid to separate off by-products, such as unconverted aminonicotinic acid, acyl chloride and the hydrochloride of the base, drying the mixture and then evaporating it down. The end products can, if required, also be purified by recrystallization or chromatography.

EXAMPLE 1

2-(3'-Trifluoromethylthiophenyl)-4H-pyrido[2,3-d][1,3]oxazin-4-one 33 parts of 3-trifluoromethylthiobenzoyl fluoride and 15 parts of triethylamine were added simultaneously to a stirred suspension of 20 parts of 2-aminonicotinic acid in 180 parts of methylene chloride at from 25° to 30° C. in the course of 10 minutes. The mixture was stirred overnight at 25° C., after which stirring was continued for a further hour at 41° C. The contents of the flask were extracted with water and twice with 1N hydrochloric acid and then evaporated down, 46 parts of 2-N-(3'-trifluoromethylthiobenzoyl)-aminonicotinic acid of melting point 138°-150° C. being obtained.

43 parts of this product in 220 parts of 1,2-dichloroethane were initially taken, and 26 parts of thionyl chloride were added. The reaction mixture was then stirred under reflux for 6 hours, cooled, and stirred into ice water. The organic phase was separated off, extracted with 10% strength sodium carbonate solution, dried, chromatographed over neutral alumina and evaporated down to give 25 parts of 2-(3'-trifluoromethylthiophenyl)-4H-pyrido[2,3-d][1,3]oxazin-4-one of melting point 141°-143° C.

EXAMPLE 2

2-(4'-Chlorodifluoromethoxyphenyl)-4H-pyrido[2,3-d][1,3]oxazin-4-one 33 parts of 4-chlorodifluoromethoxybenzoyl fluoride and 13.5 parts of -picoline were added to a stirred suspension of 20 parts of 2-aminonicotinic acid in 250 parts of 1,2-dichloroethane at from 20° to 35° C. in the course of 10 minutes. The reaction mixture was stirred for 4 hours at 25° C. and for a further 4 hours at 83° C. and then evaporated down under reduced pressure. The residue was stirred with 0.5N hydrochloric acid, and the product was filtered off under suction and washed with water and with 30 parts of methyl tert.-butyl ether, 36.9 parts of 2-N-(4'-chlorodifluoromethoxybenzoyl)-aminonicotinic acid of melting point 234°-238° C. being obtained.

15 parts of this product in 220 parts of 1,2-dichloroethane were initially taken, and 7 parts of thionyl chloride were added a little at a time at 25° C., while stirring. The reaction mixture was stirred for 4 hours at 81° C., cooled to 20° C., and stirred into 300 parts of ice water. The organic phase was separated off, extracted once with 0.5N sodium hydroxide solution, dried, chromatographed over alumina and evaporated down to give 12 parts of 2-(4'-chlorodifluoromethoxyphenyl)-4H-pyrido[2,3-d][1,3]oxazin-4-one of melting point 111°–115° C.

The following pyrido-oxazine derivatives of the formula I can be prepared by similar methods.

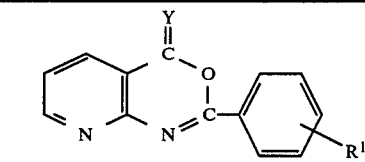

| Compound no. | R¹ | Y | M.p. [°C.] |
|---|---|---|---|
| 3 | 3-Cl | O | |
| 4 | 4-Cl | O | |
| 5 | 3-F | O | 134–135 |
| 6 | 4-F | O | 198–200 |
| 7 | 3-F | S | |
| 8 | 2-F | O | |
| 9 | 3-Br | O | |
| 10 | 4-Br | O | |
| 11 | 4-I | O | |
| 12 | 3-I | O | |
| 13 | 3-CF₃ | O | 179–182 |
| 14 | 4-CF₃ | O | 164–166 |
| 15 | 4-CF₃ | S | |
| 16 | 3-CH₂—CF₃ | O | |
| 17 | 3-CH(CF₃)₂ | O | |
| 18 | 4-CH(CF₃)₂ | O | |
| 19 | 3-O—CH₂Cl | O | |
| 20 | 4-O—CH₂Cl | O | |
| 21 | 3-O—CHF₂ | O | |
| 22 | 3-O—CHF₂ | O | 123–125 |
| 23 | 4-O—CHF₂ | O | 159–161 |
| 24 | 2-O—CHF₂ | O | |
| 25 | 3-O—CHF₂ | S | |
| 26 | 3-O—CF₂Cl | O | 104–107 |
| 27 | 3-O—CF₂Cl | S | |
| 28 | 2-O—CF₂Cl | O | |
| 29 | 4-O—CF₂Cl | S | |
| 30 | 3-O—CFCl₂ | O | |
| 31 | 3-O—CF₃ | O | 142–144 |
| 32 | 4-O—CF₃ | O | 130–132 |
| 33 | 3-O—CF₃ | S | |
| 34 | 4-O—CCl₃ | O | |
| 35 | 3-O—CF₂—CF₂H | O | 147–148 |
| 36 | 4-O—CF₂—CF₂H | O | 139–140 |
| 37 | 4-O—CF₂—CF₂H | S | |
| 38 | 3-O—CF₂—CHFCl | O | 139–141 |
| 39 | 4-O—CF₂—CHFCl | O | |
| 40 | 3-O—CF₂—CHFBr | O | |
| 41 | 3-O—CF₂—CHF—CF₃ | O | |
| 42 | 4-O—CF₂—CHF—CF₃ | O | |
| 43 | 3-O—CF₂—CF₃ | O | |
| 44 | 3-O—CH(CF₃)₂ | O | |
| 45 | 3-CF₂Cl | O | |
| 46 | 4-CF₂Cl | O | |
| 47 | 3-CFCl₂ | O | |
| 48 | 4-CFCl₂ | O | |
| 49 | 3-S—CHF₂ | O | |
| 50 | 4-S—CHF₂ | O | |
| 51 | 3-S—CHF₂ | S | |
| 52 | 4-S—CF₃ | O | 177–179 |
| 53 | 3-S—CF₃ | S | |
| 54 | 3-S—CF₂Cl | O | |
| 55 | 4-S—CF₂Cl | O | |
| 56 | 3-S—CFCl₂ | O | |
| 57 | 4-S—CFCl₂ | O | |
| 58 | 3-S—CF₂—CF₃ | O | |
| 59 | 3-S—CF₂—CF₂H | O | |
| 60 | 4-S—CF₂—CF₂H | O | |
| 61 | 3-SO₂CH₂Cl | O | |
| 62 | 4-SO₂CH₂Cl | O | |

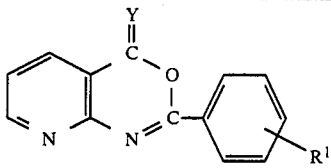

| Compound no. | R¹ | Y | M.p. [°C.] |
|---|---|---|---|
| 63 | 3-SO₂CHF₂ | O | |
| 64 | 4-SO₂CHF₂ | O | |
| 65 | 3-SO₂CF₃ | O | |
| 66 | 3-SO₂CF₃ | S | |
| 67 | 4-SO₂CF₃ | O | |
| 68 | 3-SO₂CF₂CF₃ | O | |
| 69 | 4-SO₂CF₂CF₃ | O | |
| 70 | H | O | 142–144 |
| 71 | 3-SOCF₃ | O | |
| 72 | 4-SOCF₃ | O | |

The 4H-pyrido[2,3-d][1,3]oxazin-4-one derivatives of the formula Ia may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably from 0.5 to 90, wt % of active ingredient.

The active ingredients, or agents containing them, may be applied pre- or postemergence. If certain crop plants tolerate the active ingredients less well on postemergence treatment, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.05 to 5 kg/ha, but is preferably from 0.25 to 4 kg/ha.

The action of 4H-pyrido[2,3-d][1,3]oxazin-4-one derivatives of the formula Ia on plant growth is demonstrated in greenhouse experiments.

The vessels employed were plastic flowerpots having a volume of 300 cm$^3$, and which were filled with a sandy loam containing about 3.0% humus.

For the postemergence treatment, either plants which had been sown directly in the pots and grown there were selected, or plants which had been grown from seedlings and were transplanted to the pots a few days before treatment. The plants were first grown in the vessels to a height of from 3 to 15 cm, depending on growth form, before being treated with the formulated active ingredients, which were suspended or emulsified in water as vehicle and sprayed through finely distributing nozzles. The application rates for postemergence treatment varied, depending on the active ingredient, and were, for example, 3.0, 1.0, 0.5 and 0.125 kg of active ingredient per hectare.

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plant species used in the experiments were *Avena sativa, Beta vulgaris, Centaurea cyanus,* Chrysanthemum spp., *Chrysanthemum coronarium, Euphorbia heterophylla, Galium aparine, Lamium amplexicaule, Mercurialis annua, Polygonum aviculare, Solanum nigrum, Triticum aestivum,* Veronia spp., and *Zea mays.*

On postemergence application of 3.0 kg/ha, for example compounds nos. 14, 32 and 36 had a considerable herbicidal action on broadleaved plants, whereas oats as an example of a crop plant remained completely undamaged. Benzoxazinone-based comparative agents diclosed in U.S. Pat. No. 3,914,121 and EP-A No. 17,931 had hardly any herbicidal action.

In sugar beets and Indian corn, unwanted broadleaved plants were combatted well at a rate of 1.0 kg/ha of, for instance, compounds nos. 14 and 15, without causing any appreciable damage to crop plants. A comparative agent disclosed in U.S. Pat. No. 3,914,121 caused massive damage to sugar beets and had a considerably lower herbicidal action.

For example compound no. 32, applied at a rate of 0.5 kg/ha, was suitable for combatting a broad spectrum of unwanted plants in wheat and Indian corn. The active ingredient was tolerated well by both crop plants.

Compound no. 2 selected by way of example combatted, when applied postemergence at a rate of 0.125 kg/ha, unwanted broadleaved weeds. Sugar beets were damaged to an acceptable extent. A comparative agent disclosed in EP-A No. 17,931 had a herbicidal action on sugar beets.

In view of the good compatibility of the active ingredients and the many application methods possible, the active ingredients of the formula Ia, or agents containing them, may be used not only in the crop plants tested in the greenhouse experiments, but also in a further large number of crops for removing unwanted plants.

The following crops may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |

| Botanical name | Common name |
| --- | --- |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana. tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the 4H-pyrido[2,3-d][1,3]oxazin-4-one derivatives of the formula Ia, or their salts, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc., and others.

A number of active ingredients which, when combined with the novel active ingredients, give mixtures suitable for use in various fields are given below by way of example:

3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1methylethyl)-2,1,3-benzothiadiazin-4-(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N,N-di-n-propyl-2,6-dinitro-3-amino-4-trifluoromethylaniline
N,N-di-n-propyl-2,6-dinitro-4-methylaniline
N,N-di-n-propyl-2,6-dinitro-4-methylsulfonylaniline
N,N-di-n-propyl-2,6-dinitro-4-aminosulfonylaniline
N,N-di-β-chloroethyl-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamat
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate 3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-ethylhexahydro-1-H-azepine-1-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
alpha,alpha-dichloropropionic acid, sodium salt
alpha,alpha-dichlorobutyric acid, sodium salt
alpha,alpha,beta,beta-tetrafluoropropionic acid, sodium salt
alpha-methyl-alpha,beta-dichloropropionic acid, sodium salt
methyl alpha-chloro-beta-(4-chlorophenyl)-propionate
methyl alpha,beta-dichloro-beta-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2', 4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3', 5'-dichloropyridyl-2-oxy)-phenoxy]-propionic acid, sodium salt
ethyl 2-(N-benzoyl-(3,4-dichlorophenyl)-amino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-isopropyl-5-bromo-6-methyluracil
3-sec.butyl-5-bromo-6-methyluracil
3-cyclohexyl-5,6-trimethyleneuracil
2-methyl-4-(3'-trifluoromethylphenyl)-tetrahydro-1,2,4-oxa-diazine-3,5-dione
2-methyl-4-(4'-fluorophenyl)-tetrahydro-1,2,4-oxadiazine-3,5--dione
3-amino-1,2,4-triazole
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methylpropyn-2-yl)-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(pyrazolyl-methyl)-2-chloroacetanilide
2,6-dimethyl-N-(pyrazolyl-methyl)-2-chloroacetanilide
2,6-dimethyl-N-(4-methylpyrazolyl-methyl)-2-chloroacetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-(n-butoxymethyl)-2-chloroacetanilide
2,6-diethyl-N-ethoxycarbonylmethyl-2-chloroacetanilide
2,3-dimethyl-N-isopropyl-2-chloroacetanilide
2,6-diethyl-N-(2-n-propoxyethyl)-2-chloroacetanilide
alpha-(2-methyl-4-chlorophenoxy)-N-methoxyacetamide
2-(alpha-naphthoxy)-N,N-diethylpropionamide
2,2-diphenyl-N,N-dimethylacetamide
alpha-(3,4,5-tribromopyrazol-1-yl)-N,N-dimethylpropionamide
N-(1,1-dimethylprop-2-ynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
0-(methylaminosulfonyl)-glycolic acid hexamethylene imide
2,6-dichlorothiobenzamide
2,6-dichlorobenzonitrile 3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts) pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-isopropylcarbamoyloxyphenyl)-4-methyl-1,2,4-oxadiazolidine-3,5-dione
2-pheny-3,1benzoxazinone-(4)
3-(4-bromophenyl)-3,4,5,9,10-pentaazatetracyclo-[5,4,1,0$^{2,6}$,0$^{8,11}$]-dodeca-3,9-diene
2-ethoxy-2,3-dihydro-3,3-dimethyl-5-benzofuranylmethane sulfonate
2-methyl-4,6-dinitrophenol (salts, esters)
3-(4-chlorophenyl)-3,4,5,9,10-pentaazatetracyclo-[5,4,1,0$^{2,6}$,0$^{8,1}$]-dodeca-3,9-diene
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(alpha,alpha-dimethylbenzyl)-3-(4-methylphenyl)-urea
1-phenyl-3-(2-methylcyclohexyl)-urea
1-(4-chlorophenyl)-3,3-dimethylurea
1-(4-chlorophenyl)-3methyl-3-but-1-yn-3-yl-urea
1-(3,4-dichlorophenyl)-3,3-dimethylurea
1-(3,4-dichlorophenyl)-3-methyl-3-n-butylurea
1-(4-isopropylphenyl)-3,3-dimethylurea
1-(3-trifluoromethylphenyl)-3,3-dimethylurea
1-(alpha,alpha-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea imidazolidin-2-one-1-carboxylic acid isobutylamide
1,2-dimethyl-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2,4-dichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl alpha-naphthoxyacetate
2-(2,4-dichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
OO-diisopropyl-5-(2-benzosulfonylaminoethyl)-phosphorodithioate
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxyamino)-butylidene]-5-(2-ethylthio-propyl)-3-hydroxycyclohex-2-en-1-one (salts)
2-[1-(N-ethoxyamino)-butylidene]-5-(2-phenylthio-propyl)-3-hydroxy-cyclohex-2-en-1-one (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-alpha,alpha,beta-trifluoro-beta-bromoethoxyphenyl)-3-(2H)-pyridazinone
2,4-dichloro-3'-[2-(2-ethoxy-ethoxy)-ethoxy]-4'-nitrodiphenyl ether
2,3-dihydro-3,3-dimethyl-5-benzofuranyl-ethane sulfonate
N-[4-methoxy-6-methyl- 1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1(-4-[2-(4-methylphenyl)-ethoxy]-phenyl)-3-methyl-3-methoxyurea
2,6-dimethyl-N-(pyrazol-methylenoxymethyl)-2-chloroacetanilide
2-methyl-6-ethyl-N-(pyrazolyl-methylenoxymethyl)-2-chloroacetanilide
alpha-2,4-dichlorophenoxy-propionic acid)-(3-methoxycarbonyl-amino)-anilide
1-(alpha-2-bromo -4-chlorophenoxypropionic acid)-3-(O-methylcarbamoyl)-anilide
2-methyl-ethyl-N-(pyrazolyl-ethylenoxymethyl)-2-chloro-acetanilide
2-(3-trifluoromethylphenyl)-4H-3,1-benzoxazin-4-one
2-(3-pentafluoroethoxyphenyl)-4H-3,1-benzoxazin-4-one
2-(3-trifluoromethylthio-phenyl)-4H-3,1-benzoxazin-4-one
2-(3-difluorochloromethoxyphenyl)-4H-3,1-benzoxazin-4-one
5-nitro-2-(3-trifluoromethyl-phenyl)-4H-3,1-benzoxazin-4-one
5-chloro-2-(3-trifluoromethoxyphenyl)-4H-3,1-benzoxazin-4-one
5-chloro-2-(3-alpha,alpha,beta,beta-tetrafluoroethoxyphenyl)-4H-3,1-benzoxazin-4-one
5-fluoro-2-(3-alpha,alpha,beta,beta-tetrafluoroethoxyphenyl)-4H-3,1-benzoxazin-4-one
5-chloro-2-(4-difluorochloromethoxyphenyl)-4H-3,1-benzoxazin-4-one
5-fluoro-2-(4-difluorochloromethoxyphenyl)-4H-3,1-benzoxazin-4-one
5-fluoro-2-phenyl-4H-3,1-benzoxazin-4-one
5-fluoro-2-(3-difluoromethoxyphenyl)-4H-3,1-benzoxazin-4-one
5-chloro-2-phenyl-4H-3,1-benzoxazin-4-one
methyl N-3-chloro-4-isopropylphenyl-thiolcarbamate
6-methyl-3-methoxy-5,6-dihydro-,1,2,4,6-thiatriazin-5-one-1,1-dioxide, sodium salt
6-methyl-3-ethoxy-5,6-dihydro-1,2,4,6-thiatriazin-5-one-1,1-dioxide
5-amino-4-chloro-2-phenyl-3(2H)-pyridazinone
5-amino-4-bromo-2-phenyl-3(2H)-pyridazinone
5-methylamino-4-chloro-2-(3-trifluoromethylphenyl)-3(2H)-pyridazinone
5-methylamino-4-chloro-2-(3-alpha,alpha,beta,beta-tetra-fluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
1-[3'-(2"-chloro-4"-trifluoromethylphenoxy)]-phenyl-4,5-dimethoxy-pyridazin-6-one
1-[4'-(3"-trifluoromethyl-phenoxy)]-phenyl-4,5-dimethoxy-pyridazin-6-one
methyl N-[4-(4'-methoxy-phenoxy)-3-chlorophenyl]-carbamate
methyl N-[4-(4'-difluoromethoxy-phenoxy)-3-chlorphenyl]-thio-carbamate
methyl N-[4-(4'-difluoromethoxy-phenoxy)-phenyl]thio-carbamate
1[4-(4'-methylphenylpropyl)-phenyl]-3-methyl-3-methoxyurea
1-[3-(4'-chlorophenyl-propyl)-phenyl]-3-methyl-3-methoxyurea
1-[4-(3-phenyl-2-methyl-propyl)-phenyl]-3-methyl-3-methoxyurea
1-[4-(3-(4'-chlorophenyl)-2-methyl-propyl)-phenyl]-3-methyl-3-methoxyurea
1-[4-(3-(4'-methylphenyl)-2-methylpropyl)-phenyl]-3-methyl-3-methoxyurea
2-[1-(N-ethyloxyamino)-butylidene]-5-(4-ethylphenyl)-3-hydroxy-cyclohexen-(2)-one-(1) (salts)
2-[1-(N-ethyloxyamino)-butylidene]-5-(4-fluorophenyl)-3-hydroxy-cyclohexen-(2)-one-(1) (salts)
2-[1-(N-ethyloxyamino)-butylidene-5-(4-chlorophenyl)-3-hydroxy-cyclohexen-(2)-one-(1) (salts)
methyl 2'-(2,4,6-trichlorophenyl)-hydrazino-2-cyanoacrylate
2-[1-(N-ethyloxyamino)-butylidene]-5-(1,3,3-trimethyl-cyclohexen-1-yl-2)-3-hydroxy-cyclohexen-(2)-one-(1) (salts)
2-[1-(N-ethyloxyamino)-butylidene]-5-(2,4,4-trimethyl-cyclohexen-1-yl-3)-3-hydroxy-cyclohexen-(2)-one(1) (salts)
2-[1-(N-3-chloroallyl-oxamino)-butylidene-5-(1-methyl-cyclohex-1-en-4yl)-3-hydroxy-cyclohexen-(2)-one-(1) (salts)
3-isobutoxy-5-methyl-4-methoxycarbonyl-pyrazole
5-amino-1-(2,4,6-trichlorophenyl)-4-cyano-pyrazole
5-amino-1-(2,4,6-tribromophenyl)-4-cyano-pyrazole
5-amino-1-(2,4,6-trichlorophenyl)-4-methoxycarbonyl-pyrazole
5-amino-(2,4-dichloro-6-bromophenyl)-4-methoxycarbonyl-pyrazole
5-amino-(2,6-dichloro-4-bromophenyl)-4-methoxycarbonyl-pyrazole
5-chloro-2-(3-trifluoromethyl-phenyl)-4H-3,1-benzoxazin-4-one
5-fluoro-2-(3-trifluoromethyl-phenyl)-4H-3,1-benzoxazin-4-one
2-(3-tetrafluoroethoxyphenyl)-4H-3,1-benzoxazin-4-one
5-chloro-2-(4'-fluorophenyl)-4H-3,1-benzoxazin-4-one
5-fluoro-2-(4'-fluorophenyl)-4H-3,1-benzoxazin-4-one
5-fluoro-2-(3'fluorophenyl)-4H-3,1-benzoxazin-4-one
5-chloro-2-(3'-fluorophenyl)-4H-3,1-benzoxazin-4-one
5-chloro-2-(3'-difluorochlormethylphenyl)-4H-3,1-benzoxazin-4-one 5-fluoro-2-(3'-difluorochlormethylphenyl)-4H-3,1-benzoxazin-4-one
6-methyl-3-methoxy-5-(4'-nitrophenoxy)-6H-1,2,4,6-thiatriazine-1,1-dioxide
6-methyl-3-methoxy-5-(propargyloxy-6H-1,2,4,6-thiatriazine-1,1-dioxide
6-methyl-3-methoxy-5-(2,4-dichlorobenzoxy)-6H-1,2,4,6-thiatriazine-1,1-dioxide
2-(2',4'-dichlorophenoxy)-2-fluoropropionic acid (salts, esters)
butyl 2-[4-(5'-trifluoromethylpyridyl-2-oxy)-phenoxy]-propionate
2-[4-(3'-chloro-5'-trifluoromethylpyridyl-2-oxy)-phenoxy]-propionic acid (salts, esters)
pentyl 2-[4-(6-chloroquinoxalyl-2-oxy)-phenoxy]-propionate
methyl 2-[4-(6-chloroquinoxalyl-2-oxy)-phenoxy]-propionate
2-[4-(6-chlorobenzthiazolyl-2-oxy)-phenoxy]-propionic acid (salts, esters)
2-[4-(6-chlorobenzoxazolyl-2-oxy)-phenoxy]-propionic acid (salts, esters)
1-[5-(3-fluorobenzylthio)-thiadiazolyl-2]-1-methylurea
2-methoxycarbonyl-N-(3,5-dimethylpyrimidinyl-2-aminocarbonyl)-benzole sulfonamide
alpha-(3,5,6-trichloropyrid-2-yl-oxy)-acetic acid (salts, esters)
alpha-(4-amino-3,5-dichloro-6-fluoro-pyrid-2-yl-oxy)-acetic acid (salts, esters)
S-[N-(4-chlorophenyl)-N-isopropyl-carbamoyl-methyl]-O,O-dimethyl-dithiophosphate
ammonium-(3-amino-3-carboxy-propyl)-methylphosphinate
(hydroxy)-(methyl)-phosphinyl-L-alpha-aminobutyryl-L-alanyl, sodium salt
4-trifluoromethyl-diphenyl ether
2-(3,5-dichlorophenyl)-2-(2'2'2'-trichloroethyl)-oxirane
2,4-diamino-5-methylthio-6-chloropyrimidine
N-(4-ethylthio-2-trifluoromethyl-phenyl)-methylsulfonamide
3-methoxy-4-methyl-5-(3-methyl-2-butenyloxy)-1,2-di(-hydroxymethyl)-benzole
2-(3,5-dimethylphenoxy)-2-(1,2,4-triazolyl-1)-acetic acid-N-tert-butylamide
2-(3,5-dichlorophenoxy)-2-(1,2,4-triazolyl-1)-acetic acid-N-tert-butylamide
3,7-dichloro-8-quinolinecarboxylic acid (salts, esters)
5-(2-chloro-4-trifluoromethyl-phenoxy)-N-(1-methoxycarbonylethoxy)-benzamide
N-[3-(1-ethyl-1-methylpropyl)-isoxazolyl-5]-2,6-dimethoxybenzamide
2'-methoxyethyl-2-[5-(2-chloro-4-trifluoromethyl-phenoxy)-2-nitrophenoxy]-propionate
methyl-6-(4-isopropyl-4-methyl-5-oxo-2-imidazolin-2-yl)-3-methylbenzoate
methyl-6-(4-isopropyl-4-methyl-5-oxo-2-imidozin-2-yl)-4-methylbenzoate
benzyltrimethylammonium chloride
1-[alpha(4-trifluoromethyl-phenoxy)-phenoxy-propionic acid]-3-(O-methylcarbamoyl)-anilide
1-dodecyl-cycloheptan-2-one
N-[2-chloro-4-methylsulfonyl-phenyl]-chloromethanesulfonamide
N-[2-bromo-4-ethylsulfonyl-phenyl]-chloromethanesulfonamide
N-[2,3-dichloro-4-(ethylsulfonyl)-phenyl]-chloromethanesulfonamide
2-[1-(N-ethoxyamino)-pyropylidene]-5-(pyrid-3-yl)-3-hydroxy-cyclohex-2-en-1-one (salts)
2,4,5-trichlorophenoxyacetic acid (salts, esters, amides)
2-[1-(N-ethoxyamino)-butylidene]-5-(tetrahydropyran-3-yl)-hydroxy-cyclohex-2-en-1-one (salts)
2-[1-(N-ethoxyamino)-butylidene]-5-(4-methyl-tetrahydropyran-3-yl)-3-hydroxy-cyclohex-2-en-1-one (salts)
2-[1-(N-ethoxyamino)-butylidene]-5-(tetrahydrotiopyran-3-hydroxy-cyclohex-2-en-1-one (salts)
2-[1-(N-ethoxyamino)-propylidene]-5-(pyrid-3-yl)-3-hydroxy-cyclohex-2-en-1-one (salts)
2-[1-(N-allyloxamino)-propylidene]-5-(pyrid-3-yl)-3-hydroxy-cyclohex-2-en-1-one
2-[1-(N-ethoxyamino)-butylidene]-5-(pyrid-3-yl)-3-hydroxy-cyclohex-2-en-1-one (salts)
2-[1-(N-allyloxamino)-butylidene]-5-(pyrid-3-yl)-3-hydroxy-cyclohex-2-en-1-one (salts)
2-[4,5-dihydro-4-methyl-4-isopropyl-5-oxo-1H-imidazol-2-yl]-3-quinolinecarboxylic acid
2-[4,5-dihydro-4-methyl-4-isopropyl-5-oxo-1H-imidazol-2-yl]-nicotinic acid, isopropylamine salt
2-chloro-2'-methyl-6'-ethyl-N-(N'-1-methoxycarbonyl)-ureido-methylacetanilide
2-chloro-2'-6'-diethyl-N-(N'-1-methoxycarbonyl)-ureido-methylacetanilide
2-chloro-2'-6'-dimethyl-N-(N'-1-methoxycarbonyl)-ureido-methylacetanilide
2-chloro-6-nitro-3-phenoxy-anilide
N-phosphonomethyl-glycine-trimethylsulfonium salt
5-(2-chloro-4-trifluoromethyl-phenoxy)-2-nitro-N-methansulfonyl-benzamide
1-ethoxycarbonyl-ethyl 5-(2-chloro-4-trifluoromethyl-phenoxy)-2-nitro-benzoate
1-[3'-(2''-chloro-4''-trifluoromethyl-phenyl-thio)-phenyl]-4,5-dimethoxy-pyrida-6-one
3-methyl-6-fluoro-5H-thiazolo[2,3-b]-quinazolin-5-one
3-methyl-2-sulfonic acid-5H-thiazolo[2,3-b]-quinazolin-5-one
3-methyl-2-bromo-5H-thiazolo[2,3-b]-quinazolin-5-one
5H-triazolo[2,3-b]-quinazolin-5-one
2-(1-ethoxyamino-butylidene)-5-cyclododeca-,1,5-dion-9-yl-cyclohex-1-en-1-one
2-(1-ethoxyamino-butylidene)-5-cyclododecyl-cyclohex-1-en-1-one
(2-trimethylsilylethyl)-5-(4'-trifluoromethyl-2'-2-chlorophenoxy)-2-nitro-benzylthioacetate
2-(2-chlorobenzyl)-4,4-dimethyl-isoxazolidin-3-one
N-[4-(3,4-dichlorobenzyloxymethyl)-phenyl]-N'-methyl-N'-methoxyurea
N-[4-(4-trifluoromethylbenzyloxymethyl)-phenyl]-N'-methyl-N'-methoxyurea
N-[3-chloro-4-(1-benzyloxyethyl)-phenyl]-N'-methyl-N'-methoxyurea
N-[4-(4-trifluoromethylbenzyloxyethyl)-phenyl]-N',N'-dimethylurea
3-(2'-chloro-4'-trifluoromethylphenoxy)-6-nitro-benzoic acid-N-methyl-sulfenamide
isopropyl 3-(2'-chloro-4'-trifluoromethylphenoxy)-6-nitro-benzenesulfenate
1-methyl-4-isopropyl-2-(2-methylbenzyloxy)-exo-7-oxabicyclo [2.2.]heptane
methyl 5-(2-chloro-4-trifluorometehylphenoxy)-2-nitro-acetophenoneoxime-O-acetate
O-(3-phenyl-6-chloropyridazin-4-yl)-S-n-octyl-thiolcarbonate
3-methyl-7-chloroquinoline-8-carboxylic acid (salts, esters)

3-ethyl-7-chloroquinoline-8-carboxylic acid (salts, esters)
2,6-diethyl-N-(but-2-ynyl)-2-chloroacetanilide
2-chloro-4-trifluoromethyl-3'-[3''-carboxy-propionyl)-hydrazino]-4'nitro-diphenylether (sodium salt)
N-[(4-chloro-6-methoxy-pyrimidin-2-yl)-aminocarbonyl]-2-ethoxycarbonyl-benzene sulfonamide
N-[(4-methoxy-6-methyl-1,3,5-triazin-2-yl)-aminocarbonyl]-2-methoxy-carbonyl-benzene sulfonamide
2-[1-(N-ethoxyamino)-butylidene]-5-(4a,7,8,8a-tetrahydro-2H,5H-pyrano[4,3-b]-pyran-3-hydroxy-cyclohexen -2-one
2-[1-(N-allyloxamino)-butylidene]-5-(4a,7,8,8a-tetrahydro-2H,5H-pyrano[4,3-b]-pyran-3-yl)-3-hydroxy-cyclohexen-2-en-1-one
2-[1-(N-allyloxamino)-butylidene]-5-/3,4,4a,7,8,8a-hexahydro-2H,5H-pyrano[4,3-b]-pyran-3-yl)-3-hydroxy-cyclohexen-2-en-1one
2-1-(N-ethoxyamino)-butylidene]-5-(3,4,4a,7,8,8a-hexahydro-2H,5H-pyrano[4,3-b]-pyran-3-yl)-3-hydroxy-cyclohexen-2-en-1-one
2-[4,5-dihydro-4-methyl-4-isopropyl-5-oxo-1H-imidazol-2-yl]-5-ethyl-pyridin-3-carboxylic acid
2-(1-ethoxyamino-butylidene)-5-(5,6-dihydro-2H-1,1-dioxothiopyran-3-yl-3-hydroxy-cyclohex-2-en-1-one
2-(1-ethoxyamino-propylidene)-5-(5,6-dihydro-2H-1,1-dioxothiopyran-3-yl)-3-hydroxy-cyclohex-2-en-1-one
2-(1-propargylamino-butylidene)-5-(5,6-dihydro-2H-1,1-dioxothiopyran-3-yl)-3-hydroxy-cyclohex-2-en-1-one
methyl 3-(2'-chloro-4'-trifluoromethylphenoxy)-6-nitro-phenylglyoxylate
butyl 2-[4-(2-chloro-4-trifluoromethylphenoxy)-phenoxy]-propionate
2-carboxy-N[[(4-methoxy-6-chloropyrimidin-2-yl)-amino]-carbonyl]-benzene sulfonamide It may also be useful to apply the compounds of the formula Ia, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies.

We claim:

1. A process for combatting the growth of unwanted plants, wherein the plants or the soil are treated with a herbicidally effective amount of a 4H-pyrido[2,3-d][1,3]-oxazin-4-one derivative of the formula Ia

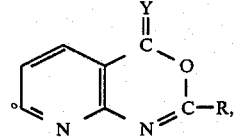

where Y is oxygen or sulfur and R is phenyl which is unsubstituted or o-, m- or p-substituted by halogen, $C_1$–$C_4$-haloalkyl, $C_1$–$C_4$-haloalkoxy, $C_1$–$C_4$-haloalkylmercapto, $C_1$–$C_4$-haloalkylsulfinyl or $C_1$–$C_4$-haloalkylsulfonyl.

2. The process of claim 1, wherein the compound of the formula Ia is 2-(4,'-trifluoromethoxyphenyl)-4H-pyrido [2,3-d][1,3]oxazin-4-one.

3. A process as defined in claim 1, wherein Y is oxygen.

4. A process as defined in claim 3, wherein R is phenyl which is unsubstituted or is o-, m- or p-substituted by halogen, $C_1$–$C_4$-haloalkyl, $C_1$–$C_4$-haloalkoxy, or $C_1$–$C_4$-haloalkylmercapto.

* * * * *